United States Patent [19]

Vestal

[11] Patent Number: 4,902,891
[45] Date of Patent: Feb. 20, 1990

[54] THERMOSPRAY METHODS AND APPARATUS FOR INTERFACING CHROMATOGRAPHY AND MASS SPECTROMETRY

[75] Inventor: Marvin L. Vestal, Houston, Tex.

[73] Assignee: Vestec Corporation, Houston, Tex.

[21] Appl. No.: 202,093

[22] Filed: Jun. 3, 1988

[51] Int. Cl.$^4$ .............................................. H01J 49/04
[52] U.S. Cl. .................................. 250/281; 250/282; 250/288
[58] Field of Search ............ 250/281, 282, 288, 288 A

[56] References Cited

U.S. PATENT DOCUMENTS

| | | | |
|---|---|---|---|
| 4,005,435 | 1/1977 | Landquist et al. | 346/75 |
| 4,647,772 | 3/1987 | Lewis et al. | 250/288 |
| 4,730,111 | 3/1988 | Vestal et al. | 250/282 |
| 4,731,533 | 3/1988 | Vestal | 250/282 |
| 4,804,839 | 2/1989 | Broadbent et al. | 250/281 |
| 4,842,701 | 6/1989 | Smith et al. | 250/281 |

OTHER PUBLICATIONS

"Direct Liquid Introduction/Thermospray Interface for Liquid Chromatography/Mass Spectrometry", Covey et al., Anal. Chem., vol. 55, No. 14, Dec. 1983, pp. 2275–2280, 250–228A.

Primary Examiner—Janice A. Howell
Assistant Examiner—Kiet T. Nguyen
Attorney, Agent, or Firm—Browning, Bushman, Anderson & Brookhart

[57] ABSTRACT

An improved thermospray vaporizer is provided for obtaining an ion vapor from a liquid sample separated by chromatography for detection or analysis by a mass spectrometer. A thermospray vaporizer comprises a capillary tube for receiving the sample, and having a jet nozzle at one end removably affixed to the capillary tube with an aperture selectively sized for a range of sample flow rates and compositions. The jet nozzle includes a generally planar sapphire insert having a cylindrical-shaped aperture of a preselected diameter. The sapphire insert is swaged into a bass holder which has a slightly larger diameter aperture than the insert. A ferrule seals between the capillary tube and an end fitting, which is welded at one end to the outer sheath of the thermospray probe and retains and end nut at the other end to secure the holder in place. The insert is thus easily replaced by removing the end nut and the brass holder with the insert. An insert with an optimum diameter aperture may thus be selected for use with the vaporizer as a function of the presumed flow rate through the vaporizer, thereby optimizing performance.

19 Claims, 1 Drawing Sheet

THERMOSPRAY METHODS AND APPARATUS FOR INTERFACING CHROMATOGRAPHY AND MASS SPECTROMETRY

BACKGROUND OF THE INVENTION

1. Field of the Invention

The present invention relates to techniques for vaporizing the eluent from a chromatography for detection or analysis and, more particularly, relates to improved thermospray techniques for vaporizing relatively low-flow rate samples separated by liquid chromatography for high sensitivity analysis by a quadrupole mass spectrometer.

2. Description of the Background

In the field of analytical chemistry, compounds separated by gas chromatography (GC) have long been analyzed by mass spectrometry (MS), since such compounds can be easily altered to an ion vapor suitable for MS analysis. Although gas chromatography is used to separate various mixtures, certain samples can only be effectively separated by liquid chromatography (LC).

Some compounds separated by liquid chromatography can be heated to vaporization and then converted to an ion vapor by bombarding the compound in its gaseous state with a beam of electrons (electron impact ionization or EI), and other compounds separated by LC can be heated to vaporization and subjected to chemically reactive ions (chemical ionization) for MS analysis. Many compounds having large, thermally labile molecules separated by LC are not, however, sufficiently volatile at ambient temperatures to form a suitable gas, and other compounds decompose when subjected to heat. Still other compounds can best be separated by supercritical fluid chromatography (SFC), a process wherein the chromatographic eluent acts much like a liquid rather than a gas.

An increasing popular technique referred to as thermospray has recently become accepted in the field of analytical chemistry for converting the eluent from the liquid chromatograph into an ionized vapor suitable for mass spectrometry analysis. A thermospray LC/MS interface is disclosed in U.S. Pat. No. 4,730,111, and hereby incorporated by reference. Thermospray interfaces are widely used today in more than 200 laboratories throughout the United States and Europe, and provide an effective technique for vaporizing the LC eluent for MS analysis. A principal advantage of this thermospray technique compared to other vaporization techniques is that non-volatile solutes separated by LC can be vaporized for MS analysis without producing uncontrolled pyrolysis of the solute, and without allowing the solute to "salt out" on solid surfaces. Moreover, various large, thermally labile molecules not amenable to conversion into an ion vapor by conventional vaporization techniques can be effectively vaporized by the thermospray techniques for MS analysis. Thus the thermospray vaporization technique is rapidly becoming a preferred technique for converting various LC eluents for MS analysis.

Thermospray may be defined as the controlled, partial vaporization, and in many instances almost but most importantly not the complete vaporization, of a liquid stream as it flows through the capillary tube of the vaporizer. In the LC/MS thermospray vaporization process, a jet of vapor is created normally containing a mist of fine particles or solvent droplets in a jetstream of vaporized gas. By partially vaporizing the solution within the capillary tube, the expanding vapor phase of the solution creates an intense vapor jet expelled at supersonic velocity from the capillary tube.

A controlled combination of a cartridge heater imbedded in a copper block which is in intimate thermal contact with the end of the capillary tube and direct ohmic heating of the tube may be used to obtain the desired constant degree of vaporization. As the droplets travel out of the capillary tube to a temperature and pressure controlled environment, they continue to vaporize due to the addition of heat to this environment from the cartridge heater and from rapid heat input from the surrounding hot vapor. As a result of heating, the liquid is nebulized and partially vaporized and any unvaporized solvent and sample are carried into the ion source as micro droplets or particles in a supersonic jet of vapor. Nonvolatile samples may be ionized by direct ion evaporation from highly charged droplets or particles, and more volatile samples may be ionized directly or by ion-molecule reactions in the gas phase. The thermospray vaporizer thus controls the partial vaporization of the sample in the probe and transits the vaporized ions through its ion exit aperture and to the mass spectrometer.

Although thermospray has significant advantages over prior art vaporization techniques for many applications, present-day thermospray technology has limited acceptance due to poor performance at low LC flow rates. Thermospray techniques are disclosed in the referenced patent have successfully been applied to conventional LC units operating at flows in the 0.5 to 2 ml per minute range, and performance is optimized under reversed-phase chromatography using volatile aqueous buffers. Conventional LC columns in the 2 mm to 5 mm range thus produce sufficient flow rates to be directly connected by existing thermospray techniques to MS. The present-day thermospray techniques are not, however, generally compatible on-line with a capillary LC or small diameter packed column LC which yield much lower flow rates. Considerable progress has recently been made in developing quality LC columns of smaller diameter, although present-day thermospray techniques do not yield a sufficient quantity of ions to the mass spectrometer for such low LC flow rates to produce satisfactory results. One solution for increasing the flow rate for existing thermospray applications is to add a favorable solvent, such as ammonium acetate, to add make-up flow downstream from the LC column. This approach has the disadvantage, however, of diluting the sample, and thus MS sensitivity decreases dramatically at low LC flow rates.

It has been recognized for some time that a reduced diameter nozzle at the end of a vaporizer capillary would allow higher temperatures and velocities at the exit of the vaporizer, while providing lower liquid velocities in the capillary where heat transfer is occurring. Accordingly, some vaporizer users have crimped the end of a vaporizer capillary with a pliers in an attempt to provide an improved vaporized jet stream. Such techniques generally do not, however, yield quality vaporizing performance for various applications, and the pattern of the jet stream is generally adversely affected by this irregular crimping operation. Since commercially available supplies of such tubing are limited in size and each size tends to have a substantially variable diameter along its length, wide variations in the effective exit diameter of the capillary tube produce inconsistent results. Moreover, conventional vaporizer capillary tubes can become plugged as a result of deposition of the non-volatile material, thereby rendering the entire vaporizer unusable for subsequent use.

Additional problems arise with the use of comparatively small diameter capillary tubes in vaporizers, particularly with respect to heat transfer and pressure drop. In tubes with similar characterists, the heat transfer efficiency is proportional to the surface area of the heated portion of the capillary tube, multiplied by the time of the contact for a given quantity of fluid. Accordingly, heat transfer efficiency is proportional to the length of the heated portion of the capillary tube and to the third power of the diameter of the capillary tube. A heated capillary tube with a diameter of 50 microns accordingly must have a heated length twenty seven times the heated length of a capillary tube with a 150 micron diameter in order to maintain the same heat transfer efficiency.

Smaller diameter capillaries also cause problems with respect to the pressure drop of the liquid through the vaporizer. For example, the total pressure required to drive 1 ml per minute of sample through a 50 micron diameter capillary in order to obtain near complete vaporization is about 200 bar. This pressure accordingly requires a substantial part of the capacity of the LC pump, so that the range of pressure drop available for the LC column is proportionally less. Also, this significant head pressure through the capillary tube makes the use of in-line auxiliary detectors less desirable.

In view of the above problems, prior art vaporizers have generally tended to utilize uniform diameter capillary tubes with the exit diameter conforming to the diameter of the capillary tube. While such prior art vaporizers provide satisfactory performance for many applications, performance is comparitively poor for vaporizers being provided with low flow rates. A practical technique for providing reliable performance from a thermospray vaporizer being supplied a liquid sample at a low flow rate is thus needed in order to enhance the versatility of the thermospray technique.

The disadvantage of the prior art are overcome by the present invention, and improved thermospray techniques are hereinafter disclosed suitable for interfacing liquid chromatography and mass spectrometry.

SUMMARY OF THE INVENTION

According to the present invention, a removable fixed nozzle is provided at the end of the capillary tube and has a substantially reduced aperture size compared to the cross-sectional area of the capillary tube. A thermospray vaporizer nozzle cross-sectional area may be selected in proportion to the mass flow rate, thereby maintaining constant thermospray conditions for a given fluid. This reduced diameter nozzle is easily replaceable, so that a nozzle having an optimized aperture diameter can be employed for different solutions and flow rates. The replaceable nozzle is comparatively inexpensive and is available in a variety of aperture sizes, so that the nozzle may be quickly and easily replaced to maximize vaporizer performance.

The jet nozzle preferably includes a planar sapphire insert having a selectively sized cylindrical-shaped aperture. The insert is mounted in a holder having a larger axially aligned aperture, so that the unitary holder and insert sub-assembly are replaced. The sapphire material of the insert is chemically, thermally, and mechanically stable and inert in the relatively harsh environment of hot vapors and corrosive fluids. A ferrule may be provided to seal the capillary tube with an end fitting, which in turn is welded to the outer sheath of the thermospray probe. The nozzle is thus sealed to the capillary tube, no leaks occur under relatively high pressures, and no "dead" volume is introduced which would cause degradation in performance.

Accordingly, it is a feature of the present invention to provide an improved thermospray vaporizer with a relatively inexpensive and easily replaceable nozzle having an exit aperture substantially restricted compared to the diameter of the capillary tube.

It is a feature of the present invention to provide a replaceable nozzle at the end of a thermospray vaporizer capillary tube fabricated from a material which is stable and relatively inert in the relatively harsh environment of the vaporizer, so that the nozzle may provide reliable performance over a relatively long life.

It is a further feature of the present invention to provide a thermospray vaporizer with a replaceable nozzle at the end of a capillary tube which may be reliably sealed with the capillary tube so that the likelihood of leaks is minimized while performance from the vaporizer is enhanced.

It is an advantage of the present invention that a thermospray vaporizer may be provided with a variety of nozzles for sealingly positioning at the end of a vaporizer capillary tube, with each of the nozzles being provided with a selectively sized and precisely known aperture diameter in order to provide high thermospray reliability from each nozzle over a selected range of sample flow rates through the vaporizer.

These and further features and advantages of the present invention will become apparent from the following detailed description, wherein reference is made to the figures in the accompanying drawings.

DETAILED DESCRIPTION OF THE PREFERRED EMBODIMENTS

Theory of Preferred Thermospray Techniques

Figure 1:
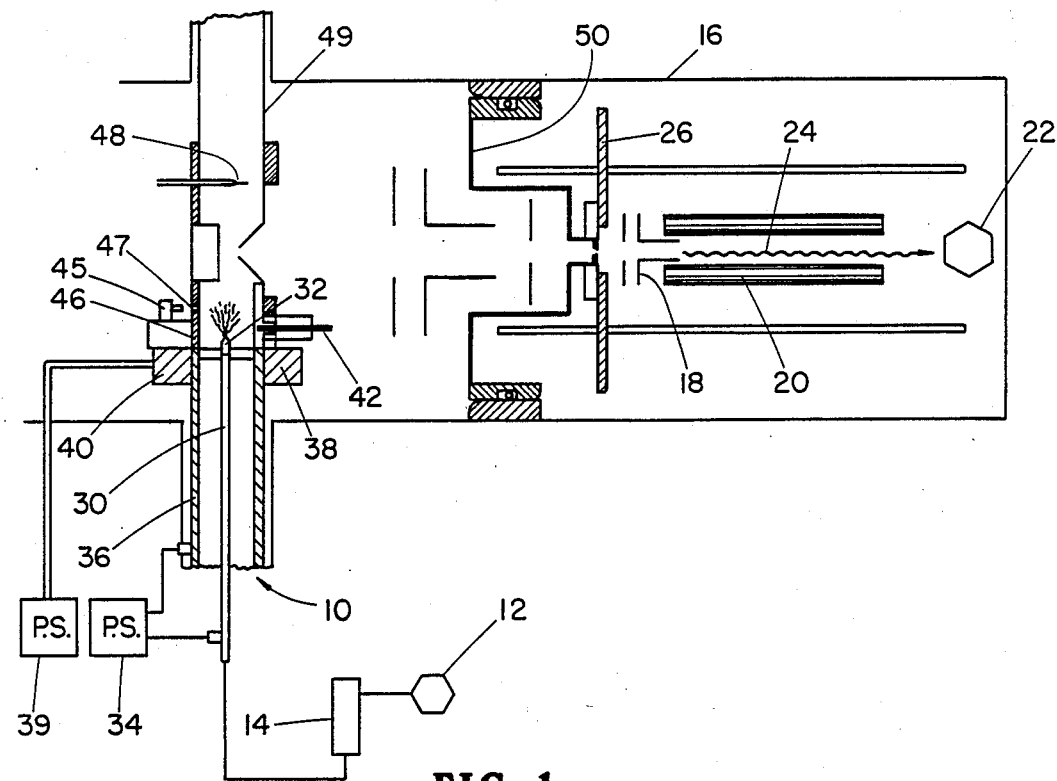
FIG. 1 is a simplified schematic diagram, partially in cross-section, of a vaporizer receiving eluent from a liquid chromatograph and supplying ion vapor to a quadrupole mass spectrometer according to the present invention.

When a liquid surface is disrupted by spraying, which occurs for example in the thermospray interfaces for chromatography/mass spectrometers, the droplets produced are often electrically charged. In thermospray, charged droplets are produced by the combination of thermospray vaporization and nebulization. To obtain maximum total ion currents, the fraction of the liquid vaporized to the point of nebulization should be as small as possible (and preferably zero). Also, the diameter of the droplets at the point of nebulization should be as small as possible, while the charge on the droplets should be as large as possible, and preferably approach the Rayleigh limit. In general, the total ion current increases with liquid flow rate through the vaporizer. The flow rate is normally fixed by the chromatograph, and thus is not generally considered an independent variable for optimizing sensitivity for LC/MC applications.

Taking the above into consideration, an ideal LC/MS interface should satisfy the following conditions: (1) sufficient heat should be supplied to complete vaporization of the liquid droplets by the time they reach the ion sampling orifice to the mass spectrometer; (2) the interface should be compatible with the use of volatile electrolytes (buffers), but such buffers should not be required for efficient ionization of a sample; (3) the interface should be applicable to polar, non-polar, volatile, non-volatile, ionic, neutral, acidic, and basic samples, and repeatable and comparable results should be obtained with the use of various solvents, including polar, non-polar, aqueous, and organic solvents; (4) no ionization source external to the vaporizer probe should be required, such as a heated filament or gaseous discharge; (5) ion intensity should be proportional to sample concentrations in the liquid; and (6) the efficiency of ion sampling into the mass spectrometer must be as high as possible (within limitations imposed by a vacuum system to remove the accompanying neutrals while maintaining an adequate vacuum in the mass analyzer).

Thermospray capillary diameters in the range of from 100 to 150 microns produce satisfactory thermospray results for LC flow rates in the range of several ml or more per minute, but poor results have been obtained for low LC flow rates using present-day thermospray techniques. In one series of tests, the vaporizer probe was heated by passing a current through the stainless steel tube, and the current level was controlled with a thermocouple attached adjacent the entrace end of the vaporizer. The thermocouple controller provided a constant power per unit flow at a given control temperature. A second thermocouple attached adjacent the exit of the vaporizer gave an approximate indication of the vapor temperature at the exit.

Plots of monitored exit temperatures as a function of input power for flow rates in the 0.05 to 2.0 ml/min range revealed that the exit temperature of a vaporizer having a large diameter capillary could be properly controlled by varying the input power, and was within the expected range. A significant variance between expected and observed exit temperature was found, however, for a vaporizer with small diameter capillaries.

It was previously assumed that the capillary vaporization velocity could be determined by:

$$V_v = \frac{P_v(T) - P_a}{\rho^\circ L} \left(\frac{m}{2\pi KT}\right)^{1/2} \quad \text{Equation 1}$$

where $V_v$ is the vaporization velocity, $P_v(T)$ is the vapor pressure of the liquid at temperature T, K is Boltzmann's constant, $P_a$ is the pressure of the vapor inside the tube at the exit, $\rho_L$ is the density of the liquid, and m is the molecular mass of the liquid. By numerically inverting the above equation, the exit temperature can be calculated as a function of liquid velocity.

It has now been determined that the above equation does not provide an adequate indication of the exit temperature, especially for small diameter capillaries of a uniform diameter to the nozzle. Particularly, it has been determined that exit temperature can be more properly calculated by:

$$\overline{V_v} = \frac{1}{\rho^\circ L}\left(\frac{m}{2\pi K}\right)^{1/2} \int_0^L \frac{P_v[T(x)] - P(x)}{[T(x)]^{1/2}} dx \quad \text{Equation 2}$$

where the integral is taken over the length of the heated capillary for which vaporization is occurring. Thus the vaporization velocity is more closely a function of the average temperature along the capillary in the region where vaporization occurs, rather than the temperature at the exit of the capillary.

It can be seen that if the pressure of the vapor inside the capillary were constant (vaporization occuring at constant pressure and temperature), Equation 2 reduces to Equation 1. Although both the exit pressure and the pressure drop in the tube are proportional to the mass flow of the vapor, the exit pressure is proportional to the square of the tube diameter and the pressure drop varies as the fourth power of the tube diameter. Thus Equation 1 is a poor approximation of exit temperatures for low flow rates through small diameter tubes (0.2 ml per minute, 50 micron diameter tube), although a reasonably good approximation of exit temperatures for larger flow rates through larger diameter tubes (1 ml per minute, 150 micron diameter tube).

From the above considerations, it has been determined that a reduction in capillary tube diameter is not the preferred technique to increase thermospray performance for lower LC flow rates. Rather, it would be preferable that the exit diameter from the vaporizer probe be substantially less than the capillary tube diameter in the heated region, so that Equation 1 remains a good approximation of exit temperature. Under these conditions, the temperature inside the vaporizer would not be significantly higher than the temperature at the exit, and most of the pressure drop would occur at the exit so that the total pressure drop for a given flow would be much lower than in the case of a tube maintaining a constant diameter to the exit. Also, by setting the desired liquid velocity at the calculated vaporization velocity, $V_v$, the desired cross-sectional capillary exit area can be calculated as a function of the flow rate, F, divided by the liquid velocity, $V_L$.

Based upon theoretical consideration and enhanced by experimental work, the optimum aperture diameter for obtaining the best performance from a thermospray vaporizer is approximately given by $$d = 75 F^{\frac{1}{2}} \quad \text{Equation 3}$$

where F is the liquid flow rate in ml per minute, and d is the nozzle diameter in microns. Experimental evidence suggests that the flow rate can be increased or decreased by a factor of two from the optimum value expressed in Equation 3 for a given nozzle diameter without seriously degrading performance, although wider variations may cause unacceptable losses in performance. Accordingly, the technique of the present invention utilizes a jet nozzle with an aperture diameter, d, selected for one or more particular applications based on the anticipated or presumed flow rate through the vaporizer, wherein the selected jet nozzle aperture is within the range of $$50 F^{\frac{1}{2}} \leq d \leq 100 F^{\frac{1}{2}} \quad \text{Equation 4}$$

The vaporizer according to the present invention thus allows the nozzle diameter to be chosen to accommodate any particular flow rate range desired for a particular application. If a substantially different flow rate through the vaporizer is subsequently anticipated or obtained, the nozzle can be readily changed to have an aperture of a diameter within the value expressed in Equation 4 for continuing to obtain reliable performance from the vaporizer.

GENERAL THERMOSPRAY VAPORIZER

A thermospray vaporizer 10 is generally shown in FIG. 1 suitable for supplying effluent on-line from a liquid chromatographic column 14 to a mass spectrometer 16. Mixtures in an unknown sample 12 are separated by conventional LC technology, and the solution is vaporized by the interface 10 in order to detect, quantify, or determine physical or chemical properties of the separates solutions and thus the sample.

Once the sample is vaporized, various techniques, such as photoionization, flameionization, electron capture, optical photometry, light scattering, light emission, atomic absorption, and other suitable techniques may be used for detecting and analyzing molecules or particles in a gaseous or vacuumed environment. Nevertheless, the thermospray vaporizer of the present invention is particularly well suited for supplying vaporizer particles to a conventional mass spectrometer for such detection and analysis.

The mass spectrometer 16 shown in FIG. 1 includes a quadrupole mass analyzer 20, and a detector 22. The ion beam 24 passes through the quadrupole analyzer 20 for scanning over a range of atomic mass units and selecting ions of a particular mass. The detector 22 at the output of the analyzer 20 produces a representation of a mass spectrum for identifying the sample 12. A conventional mounting plate 26 is shown, and an entrance lens 18 is provided with a small diameter aperture for controlling the ions which reach the analyzer 20. The mass analyzer 16 is shown in FIG. 1 is more particularly described in U.S. Pat. No. 4,731,533, which is hereby incorporated by reference. Alternatively, a quadrupole EID cell may be used for obtaining effective dissociation of ions by electron impact, coupled with a conventional quadrupole analyzer, as shown in U.S. Pat. No. 4,731,533 also hereby incorporated by reference.

Figure 2:
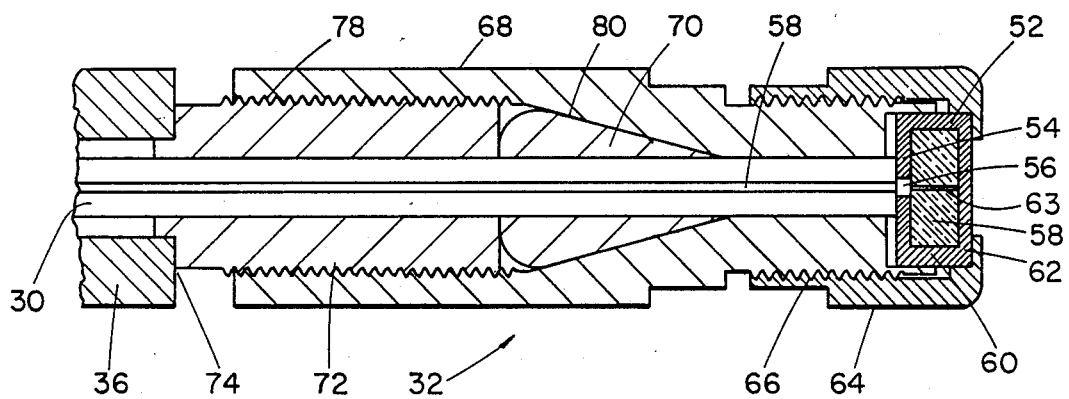
FIG. 2 is a cross-sectional view of the tip end of a vaporizer probe employing a replaceable reduced diameter nozzle according to the present invention.

The vaporizer 10 includes an elongate capillary tube 30 having a jet nozzle 32 which is shown in greater detail in FIG. 2. Liquid passing through the cylindrical interior passageway in the tube 30, which typically has a passageway diameter of approximately 150 microns, is heated according to the thermospray concept disclosed in the '111 patent so that a controlled partial vaporization of the liquid ejected from the tube is obtained. Substantially the entire length of the tube is heated by direct Joule heating from power supply 34. A circuit thus passes direct or alternating current from a power supply 34 through the length of the capillary tube 30, through the nozzle 32, and back to the power supply via the vaporizer outer sheath or tube 36. The discharge end of the tube 30 and thus the jet nozzle 32 is also preferably heated by cartridge heaters 38, 40 which are heated by power supply 39 and are in direct thermal contact with the jet nozzle 32. Further details regarding the suitable system for maintaining a constant degree of vaporization for the liquid ejected from the nozzle 32 is disclosed in the '111 patent.

Accordingly, heat is supplied to the capillary tube 30 sufficient to vaporize a preselected proportion of the liquid discharged through the jet 32. The vaporized material is ejected into the ion source 46 of the quadrupole mass spectrometer 16. An electron gun 45 passes an electron beam through entrance 47 in the ion source 46. The discharge electrode 42 provides an alternative source of ionization. A source pump out 49 is connected to a vacuum system including a vacuum pump (not shown), and a baffle 50 is conventionally provided upstream from the analyzer. Stable operation of the vaporizer may be obtained by regulating the power output from the power supplies 34, 39 in order to maintain the temperature measured by any of the sensors 48, at a constant value.

REDUCED DIAMETER CAPILLARY EXIT

A preferred embodiment of the reduced diameter nozzle 32 at the end of the capillary tube 30 for the vaporizer 10 according to the present invention is shown in FIG. 2. A replaceable metal holder 52 is provided in engagement with end surface 54 of the capillary tube 30, and has a central passageway 56 axially aligned with but having a diameter greater than the diameter of the uniform passageway 58 in the capillary tube 30. A holder 52 may be fabricated from a relatively soft metal, such as brass, to ensure reliable sealing engagement between the holder and the capillary tube, and between the holder and the sapphire insert 58. In order to reduce deleterious corrosive effects, the holder 52 may be plated with a corrosion resistant metal, such as nickel. The holder 52 has a generally U-shaped cross-sectional configuration, with the ends of the cylindrical walls 60 swagged at 62 to fixedly position and seal the insert 58 within the holder 52. Insert 58, in turn, is a generally cylindrical-shaped sapphire insert having a cylindrical-shaped passageway 64 which is also axially aligned with the passageway 58 through the tube 30, but has a diameter substantially less than the diameter of the flow path through the capillary tube 30.

Sapphire is a preferred material for the insert 58 because it is a chemically resistant material and is commerically available with apertures having selectively sized cylindrical-shaped passageways in the range of from 0.0015 to 0.006 inches. The passageways 64 in the sapphire may be formed by microdrilling techniques which produced precisely located, sharp-edge and extremely round holes. The hole may be initially laser pierced for high speed production and then the hole lapped by a charged wire technique to clean out the blasted area and open the hole to a finished polished size. The lapped hole eliminates problems of burrs, irregular contour, or jagged edges normally associated with conventional drilling techniques. Suitable microdrilled inserts for use with the present invention may have an outer diameter of 0.087 inches and a thickness of 0.047 inches, and are commercially available from Bird Precision in Waltham, Mass.

The replaceable holder 52 and an insert 58 with a selectively sized aperture 63 is held in sealed engagement with the end 54 of the stainless steel tube 30 by an end nut 64. Nut 64, in turn, is threaded at 66 for mating engagement with adaptor fitting 68. Fitting 68 is sealed against the capillary tube 30 by a stainless steel ferrule 70. Member 72 may be welded at 74 for fixed and sealed engagement with the outer sheath 36 of the thermospray probe which houses the capillary tube 30. Alternatively, the ferrule 70 and member 72 can be machined from a single piece of stainless steel. Threads 78 on the member 72 cooperate with the corresponding threads on the adaptor fitting 68 to fix the position of the fitting 68 with respect to the sheath 36, while the frusto-conical interior surface 80 on the adaptor fitting cooperates with the ferrule 70 to seal the capillary tube and the fitting 68. Ferrule 70 also cooperates with the surface 80 on the adaptor 68 to maintain axial alignment of the capillary tube 30 and the adaptor 68, and thus proper axial alignment of the passageway 64 in the insert 58 with respect to the flow passageway in the capillary tube 30. In order to replace the sapphire insert 58 with another insert having a preselected diameter passageway 64, the nut 64 may simply be unthreaded from the adaptor 68, a new subassembly (consisting of a holder 52 and an insert 58) placed against the end of the capillary tube, and the nut 64 rethreaded to the adaptor 68.

It should be understood that the electrical current path for heating the capillary tube 30 along substantially its entire length passes from the capillary tube 30 to the outer sheath 36 via the member 72. Accordingly, the extreme end of the capillary tube 30, e.g. the last one quarter inch of the capillary tube, adjacent the insert 58 is not heated by electrical energy, but rather is heated by direct thermal contact between the heater blocks shown in FIG. 1 and described previously. The outer diameter of the end nut 64 and the outer diameter of the adaptor 68 are thus maintained to coinicide with the outer diameter of the sheath 36, so that the end of the probe may be inserted a desired distance into the cylindrical passageway of suitable block heaters 38, 40 shown in FIG. 1 to maintain the end of the capillary tube 30 at the desired temperature which will achieve the controlled partial vaporization of the solution.

Other techniques have been considered for providing the restriction at the end of the capillary tube, but do not fully satisfy the purposes of the present invention as well as the embodiment shown in FIG. 2 and described above. Inserts with lazer-drilled diaphrams of stainless steel have been considered and are commercially available, and such stainless steel diaphrams may be adequately sealed against the end of the capillary tube 30. However, the apertures in such stainless steel diaphrams tend to rapidly erode when used as a thermospray nozzle for most vaporizer applications, and accordingly satisfactory performance over a long period of time is difficult to maintain. Although a satisfactory jet nozzle can also be produced by swagging or crimping the end of a stainless steel capillary tube, both the stability and reproduceability of such tubes is generally considered unsatisfactory. Moreover, this latter embodiments does not offer a predetermined technique of the present invention wherein the nozzle is easily replaceable with other nozzles of precisely located and selectively sized apertures.

The techniques of the present invention thus allows a thermospray operator to easily change the aperture diameter at the exit of a vaporizer, and thus optimize spraying techniques. According to the present invention, the cross-sectional area of passageway through the selected exit nozzle of the thermospray vaporizer may be reduced in proportion to the mass flow through the vaporizer capillary, so that constant conditions can be maintained for the thermospray vaporization process. By properly reducing the capillary tube exit diameter for low LC flow rates, a reduction of minimum sample requirements for satisfactory MS analysis by at least 1 or 2 orders of magnitude should be obtained. This technique should yield an ionization production rate which is directly proportional to the flow rate.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A thermospray vaporizer for obtaining an ion vapor for detection or analysis by a mass analyzer from a liquid sample having molecules of interest separated by chromatography, the vaporizer comprising:
   a metal capillary tube having an internal cylindrical passageway for transmitting the liquid sample to a discharge end thereof;
   a heater for partially vaporizing the liquid smaple passing through the passageway in the metal capillary tube;
   a controller for controlling the temperature of the liquid sample passing through the passageway in the capillary tube to maintain a constant degree of partial vaporization of the sample molecules discharged from the capillary tube and for producing an intense thermospray jet of vaporized ions and minute particles entrained in the vaporized jet;
   a jet nozzle being removably affixed to the capillary tube at the discharge end thereof and having an aperture cross-sectional area substantially less than the cross-sectional area of the passageway in the capillary tube; and
   the aperture of the jet nozzle being selectively sized as a function of sample flow rates to satisfy the relationship $50F^{\frac{1}{2}} \leq d \leq 100F^{\frac{1}{2}}$, wherein d is the aperture diameter in microns, and F is the sample flow rate in milliliters per minute.

2. A vaporizer as defined in claim 1, wherein the jet nozzle comprises:
   a planar disk having the aperture axially aligned with the cylindrical passageway in the capillary tube; and
   the planar disk being removably fixed to and in sealed engagement with a planar end surface of the capillary tube normal to a central axis of the capillary tube.

3. A vaporizer as defined in claim 2, further comprising:
   a holder for fixing the planar disk relative to the capillary tube and having an axially aligned aperture with a cross-sectional area substantially greater than the passageway in the capillary tube; and
   the planar disk is fixedly positioned within the holder.

4. A vaporizer as defined in claim 1, wherein the jet nozzle has a selectively sized aperture for producing a jet at approximately vaporization velocity.

5. A vaporizer as defined in claim 1, further comprising:
   an outer sheath substantially enclosing the capillary tube; and
   an end nut securable to the outer sheath to retain the jet nozzle in engagement with the capillary tube and for selectively disconnecting from the outer sheath to remove and replace the jet nozzle.

6. A vaporizer as defined in claim 5, further comprising:
an adaptor fitting securable to the outer sheath and having a through port for receiving the capillary tube and having threads for mated engagement with the end nut; and
a sealing member for sealing between the adaptor fitting and the capillary tube radially within the adaptor fitting.

7. A vaporizer as defined in claim 6, wherein:
the adaptor fitting has a frusto-conical sealing surface; and
the sealing member is a ferrule member positioned radially between the capillary tube and the frusto-conical sealing surface of the adaptor fitting.

8. A vaporizer as defined in claim 5, wherein:
the heater includes a tip heating member having a cylindrical-shaped through port for direct thermal heating of the jet nozzle; and
an outer diameter of the end nut and an outer diameter of the adaptor fitting are each substantially identical to a diameter of the cylindrical-shaped through port for direct thermal heating of end nut and adapter fitting.

9. A vaporizer as defined in claim 8, wherein the outer diameter of the capillary tube and the outer diameter of the adaptor fitting are substantially identical to the outer diameter of the sheath, such that the tip heating member may be selectively moved axially with respect to the sheath.

10. A thermospray vaporizer for obtaining an ion vapor from a liquid sample for detection or analysis by a mass analyzer, the vaporizer comprising:
capillary tube means having an internal passageway for transmitting the liquid sample to a discharge end thereof;
heating means for partially vaporizing the liquid sample passing through the passageway in the capillary tube means;
control means for controlling the temperature of the liquid sample passing through the passageway in the capillary tube means to maintain a constant degree of partial vaporization of the sample molecules discharged from the capillary tube means; and
jet nozzle means being removably affixed to the capillary tube means at the discharge end thereof and having an aperture cross-sectional area substantially less than the cross-sectional area of the passageway in the capillary tube means, whereby an aperture area of the jet nozzle is selectively sized as a function of sample flow rates to produce a thermospray jet of approximately vaporization velocity.

11. A vaporizer as defined in claim 10, wherein the jet nozzle means comprises:
a planar disk having the aperture axially aligned with the passageway in the capillary tube means; and
the planar disk being removably fixed to and in sealed engagement with a planar end surface of the capillary tube means normal to the central axis of the capillary tube means.

12. A vaporizer as defined in claim 11, further comprising:
a holder for fixing the planar disk relative to the capillary tube means and having an axially aligned aperture with a cross-sectional area substantially greater than the cross-sectional area of the passageway in the capillary tube means; and
the planar disk is fixedly positioned within the holder.

13. A vaporizer as defined in claim 10, further comprising:
an outer sheath substantially enclosing the capillary tube means; and
an end nut securable to the outer sheath to retain the jet nozzle with engagement with the capillary tube means and for selectively disconnecting from the outer sheath to remove and replace the jet nozzle means.

14. A vaporizer as defined in claim 13, further comprising:
an adaptor fitting having a through port for receiving the capillary tube means and securable to the outer sheath, the adaptor fitting having threads for mated engagement with the end nut and having a frusto-conical sealing surface; and
a ferrule sealing member for sealing between the adaptor fitting and the capillary tube means.

15. A vaporizer as defined in claim 13, wherein:
the heating means includes a tip heating member having a cylindrical-shaped through port for direct thermal heating of the jet nozzle means; and
an outer diameter of the end nut and an outer diameter of the outer sheath are substantially identical for positioning within the cylindrical-shaped through port of the tip heating member.

16. An improved thermospray method for producing an ion vapor for detection or analysis by an analyzer from a liquid sample having molecules of interest separated by chromatography, the method comprising:
providing a metal capillary tube have an internal passageway for transmitting the liquid sample to a discharge end thereof;
heating the liquid sample passing through the capillary tube to partially vaporize the liquid sample discharged from the capillary tube;
controlling the temperature of the sample within the capillary tube to maintain a constant degree of partial vaporization of the sample molecules discharged from the capillary tube and for producing an intense thermospray jet of vaporized ions and minute particles entrained in a vaporized jet;
selecting a jet nozzle having a cross-sectional area aperture as a function of the anticipated-liquid sample flow rate through the capillary tube; and
removably positioning the jet nozzle at the end of the capillary tube having the aperture of a selected cross-section area which is substantially less than the cross-sectional area of the passaway in the capillary tube.

17. The vaporizer as defined in claim 10, wherein the selected jet nozzle aperture satisfies the relationship $50F^{\frac{1}{2}} \leq d \leq 100F^{\frac{1}{2}}$, wherein d is the aperture diameter in microns, and F is the sample flow rate in milliliters per minute.

18. The vaporizer as defined in claim 17, wherein the selected jet nozzle aperture has a diameter of from 0.0015 inches to 0.006 inches, and the selected jet nozzle has a thickness substantially greater than the selected jet nozzle aperture diameter.

19. An improved thermospray method as defined in claim 16, wherein the step of selecting the jet nozzle comprises:
selecting the jet nozzle having the aperture cross-sectional area which satisfies the relationship $50F^{\frac{1}{2}} \leq d \leq 100F^{\frac{1}{2}}$, wherein d is the aperture diameter in microns, and F is the sample flow rate in milliliters per minute.

* * * * *

UNITED STATES PATENT AND TRADEMARK OFFICE
CERTIFICATE OF CORRECTION

PATENT NO. : 4,902,891

DATED : February 20, 1990

INVENTOR(S) : Marvin L. Vestal

It is certified that error appears in the above-identified patent and that said Letters Patent is hereby corrected as shown below:

In Column 1, line 5, insert:

--<u>Government Support</u>

The invention described herein was made in part during the performance of work under grant number GM 37313 from the Department of Health and Human Services, and the United States Government has a nonexclusive, nontransferable, irrevocable, paid-up license to practice this invention throughout the world.--

Signed and Sealed this

Thirty-first Day of December, 1991

*Attest:*

HARRY F. MANBECK, JR.

*Attesting Officer*     *Commissioner of Patents and Trademarks*